United States Patent
Wilk (10) Patent No.: US 8,016,839 B2
(45) Date of Patent: Sep. 13, 2011

(54) INTRA-ABDOMINAL MEDICAL PROCEDURES AND DEVICE

(75) Inventor: Peter J. Wilk, New York, NY (US)

(73) Assignee: Wilk Patent, LLC, New York, NY (US)

(*) Notice: Subject to any disclaimer, the term of this patent is extended or adjusted under 35 U.S.C. 154(b) by 958 days.

(21) Appl. No.: 11/336,614

(22) Filed: Jan. 20, 2006

(65) Prior Publication Data

US 2006/0200004 A1 Sep. 7, 2006

Related U.S. Application Data

(60) Provisional application No. 60/647,365, filed on Jan. 26, 2005.

(51) Int. Cl.
*A61B 17/26* (2006.01)
(52) U.S. Cl. .................... 606/114; 606/128
(58) Field of Classification Search ............ 600/184, 600/208; 604/513, 539, 288.01, 288.02, 604/288.03; 606/114, 128; 128/898
See application file for complete search history.

(56) References Cited

U.S. PATENT DOCUMENTS

| | | | | |
|---|---|---|---|---|
| 4,705,040 A * | 11/1987 | Mueller et al. | ............... | 606/108 |
| 5,074,867 A * | 12/1991 | Wilk | ............... | 606/128 |
| 5,211,624 A | 5/1993 | Cinberg et al. | | |
| 5,246,424 A * | 9/1993 | Wilk | ............... | 604/164.03 |
| 5,297,536 A * | 3/1994 | Wilk | ............... | 600/104 |
| 5,354,270 A | 10/1994 | Wilk et al. | | |
| 5,374,273 A * | 12/1994 | Nakao et al. | ............... | 606/127 |
| 5,458,131 A * | 10/1995 | Wilk | ............... | 600/105 |
| 5,735,289 A | 4/1998 | Pfeffer et al. | | |
| 5,891,113 A * | 4/1999 | Quinn | ............... | 604/526 |
| 6,299,598 B1 * | 10/2001 | Bander | ............... | 604/101.03 |
| 6,516,216 B1 * | 2/2003 | Fontenot et al. | | |
| 2001/0049497 A1 * | 12/2001 | Kalloo et al. | ............... | 604/164.01 |
| 2002/0007190 A1 * | 1/2002 | Wulfman et al. | ............... | 606/167 |
| 2002/0087153 A1 * | 7/2002 | Roschak et al. | | |
| 2003/0014076 A1 * | 1/2003 | Mollenauer et al. | ............... | 606/213 |
| 2004/0116904 A1 * | 6/2004 | Monga | ............... | 604/544 |
| 2004/0249248 A1 * | 12/2004 | Bonadio et al. | | |

OTHER PUBLICATIONS

Notification Concerning Transmittal of International Preliminary Report on Patentability from international counterpart case PCT/US2006/001956.

* cited by examiner

*Primary Examiner* — Anhtuan Nguyen
*Assistant Examiner* — David Eastwood
(74) *Attorney, Agent, or Firm* — R. Neil Sudol; Henry D. Coleman; William J. Sapone (57) ABSTRACT

Improvements in intra-abdominal surgery include a method for removing large chunks of organic or inorganic material from the abdomen through a natural body opening such as the urethra. The technique may be supplemented by laparoscopic procedures.

21 Claims, 10 Drawing Sheets

INTRA-ABDOMINAL MEDICAL PROCEDURES AND DEVICE

CROSS-REFERENCE TO RELATED APPLICATION

This application claims the benefit of U.S. Provisional Patent Application No. 60/647,365 filed Jan. 26, 2005.

BACKGROUND OF THE INVENTION

This invention relates to medical procedures carried out without the formation of an incision in a skin surface of the patient.

Such procedures are described in U.S. Pat. Nos. 5,297,536 and 5,458,131.

As described in those patents, a method for use in intra-abdominal surgery comprises the steps of (a) inserting an incising instrument with an elongate shaft through a natural body opening into a natural body cavity of a patient, (b) manipulating the incising instrument from outside the patient to form a perforation in an internal wall of the natural internal body cavity, and (c) inserting a distal end of an elongate surgical instrument through the natural body opening, the natural body cavity and the perforation into an abdominal cavity of the patient upon formation of the perforation. Further steps of the method include (d) inserting a distal end of an endoscope into the abdominal cavity, (e) operating the surgical instrument to perform a surgical operation on an organ in the abdominal cavity, (f) viewing the surgical operation via the endoscope, (g) withdrawing the surgical instrument and the endoscope from the abdominal cavity upon completion of the surgical operation, and (h) closing the perforation.

Visual feedback may be obtained as to position of a distal end of the incising instrument prior to the manipulating thereof to form the perforation. That visual feedback may be obtained via the endoscope or, alternatively, via radiographic or X-ray equipment.

The abdominal cavity may be insufflated prior to the insertion of the distal end of the endoscope into the abdominal cavity. Insufflation may be implemented via a Veress needle inserted through the abdominal wall or through another perforation in the internal wall of the natural body cavity. That other perforation is formed by the Veress needle itself. U.S. Pat. No. 5,209,721 discloses a Veress needle that utilizes ultrasound to detect the presence of an organ along an inner surface of the abdominal wall.

A method in accordance with the disclosures of U.S. Pat. Nos. 5,297,536 and 5,458,131 comprises the steps of (i) inserting an endoscope through a natural body opening into a natural body cavity of a patient, (ii) inserting an endoscopic type incising instrument through the natural body opening into the natural body cavity, (iii) manipulating the incising instrument from outside the patient to form a perforation in an internal wall of the natural internal body cavity, (iv) moving a distal end of the endoscope through the perforation, (v) using the endoscope to visually inspect internal body tissues in an abdominal cavity of the patient, (vi) inserting a distal end of an elongate surgical instrument into the abdominal cavity of the patient, (vii) executing a surgical operation on the internal body tissues by manipulating the surgical instrument from outside the patient, (viii) upon completion of the surgical operation, withdrawing the surgical instrument and the endoscope from the abdominal cavity, (ix) closing the perforation, and (x) withdrawing the endoscope from the natural body cavity.

The surgical procedures of U.S. Pat. Nos. 5,297,536 and 5,458,131 reduces trauma to the individual even more than laparoscopic procedures. Hospital convalescence stays are even shorter. There are some potential problems with the procedures, such as the difficulty in forming a fluid tight closure of the perforation formed in the wall of the hollow internal body organ. Certain intra-abdominal operations cannot be easily performed owing to the necessity or removing large chunks of organic or inorganic material (e.g., entire kidney, gall stones). Some operations can require the simultaneous usage of many different instruments so that space along the selected pathways may be difficult to find.

OBJECTS OF THE INVENTION

It is an object of the present invention to provide improvements on the afore-described surgical procedures.

A related object of the present invention is to provide intra-abdominal surgical procedures that alleviate the above-discussed problems.

It is a more specific object of the present invention to provide a method for enabling or facilitating the removal of large tissue samples or objects from a patient via a natural body cavity of the patient.

It is another object of the present invention to provide a method and/or an associated device for keeping a passageway open in an internal hollow organ.

These and other objects of the present invention will be apparent from the drawings and detailed descriptions herein. While every object of the invention is believed to be attained in at least one embodiment of the invention, there is not necessarily any single embodiment that achieves all of the objects of the invention.

SUMMARY OF THE INVENTION

A surgical method comprises, in accordance with the present invention, inserting a distal end portion of a surgical instrument into a patient through a natural body opening, through a natural body cavity of the patient naturally communicating with the natural body opening, and through a temporary artificial opening in a wall of an internal organ of the patient defining the natural body cavity. Subsequently the second surgical instrument is manipulated from outside the patient to sever at least a substantial portion of another organ of the patient. The severed organ portion is withdrawn through the artificial opening into the natural body cavity. The method further comprises inserting a distal end portion of a medical instrument through the natural body opening into the natural body cavity and operating the medical instrument from outside the patient to fractionate material included in the severed organ portion. The severed organ portion including the fractionated material is extracted from the natural body cavity through the natural body opening. Also, the distal end portions of the surgical instrument and the medical instrument are withdrawn from the patient through the natural body opening.

The surgical instrument and the medical instrument may be the same or different instruments.

The internal organ through which the operation is effectuated may be the stomach, the colon, the vagina, or the urinary bladder. Of course, the invention contemplates that multiple instruments may be inserted into the patient, particularly, the abdominal cavity, through multiple natural body cavities that communicate with the ambient environment though closable natural body openings such as the mouth, the anus or rectum, the vaginal orifice, and the urethra.

The organ which is partially severed or ablated may be virtually any organ that sits in the abdominal cavity. However, prime candidates for this operation are the uterus, the gall bladder, and the kidneys.

The medical instrument that fractionates (i.e., reduces to smaller particles or pieces) material contained or included in the severed portion of the target organ may be an ablation instrument, a morsellator, a laser tool, or an ultrasound device. Other devices may be used to accomplish the method described and claimed herein.

The entire severed organ portion may be reduced to pieces or particles in the natural body cavity and subsequently removed from the internal organ via the natural body opening. An irrigation liquid may be introduced into the natural body cavity to form a slurry for facilitating the extraction of the fractionated organ portion from the patient.

Where the target organ is the gall bladder, the material that is fractionated may be one or more gall stones. In that case, the fractionation may occur within the severed gall bladder and inside the natural body cavity of the patient. A distal tip of the medical instrument is inserted into the gall bladder inside the natural body cavity prior to the operating of the medical instrument to fractionate the gall stones.

A surgical method comprises, in accordance with a specific embodiment of the present invention, inserting a surgical instrument through a patient's urethra into the patient's urinary bladder, using the surgical instrument to form an opening through a wall of the bladder; inserting a medical instrument through the urethra, the bladder and the opening, subsequently manipulating the medical instrument from outside the patient to perform an operation inside the patient, and withdrawing the medical instrument from the patient through the opening, the bladder, and the urethra. The the surgical instrument and the medical instrument may be the same or different instruments.

A surgical device in accordance with the present invention comprises at least two connected balloon portions expandable from a collapsed configuration to an inflated configuration wherein outer surfaces of the balloon portions are in contact with respective opposing surfaces of a wall of a hollow body organ of a patient along a plane and define a through aperture with an axis extending substantially perpendicularly to the plane, the through aperture being passable by a medical instrument. This device facilitates a transluminal or transorgan medical procedure by holding open a hole in the wall of the hollow organ and providing an easily negotiated passageway or aperture for the passing of elongate medical instruments into the abdominal cavity.

The balloon portions may be independently inflatable, in which case there are at least two tubes extending to respective ones of the balloon portions. Alternatively, the balloon portions communicate with one another and are inflatable together, in which case a tube extends to at least one of the balloon portions for conducting a fluid to the balloon portions to expand the same.

Typically, the balloon portions are each annular or toroidal.

A surgical method of another embodiment of the present invention comprises inserting a distal end portion of a surgical instrument through a natural body opening of a patient into a natural body cavity of the patient, using the surgical instrument to form a temporary artificial opening through a wall of an organ defining the natural body cavity, inserting a surgical port device through the natural body opening into the natural body cavity, and subsequently disposing the port device in the artificial opening to keep the opening open. The port device defines an aperture surrounded by the artificial opening and coaxial therewith. With the port device disposed in the artificial opening, a distal end portion of a medical instrument is inserted through the natural body opening, into the natural body cavity and through the aperture in the port device.

Preferably, the port device comprises at least two balloon portions, the port device being disposed in the artificial opening so that the balloon portions are positioned on opposite sides of the internal organ wall. The disposing of the port device in the artificial opening includes inflating the balloon portions to hold the port device in the wall and to define the aperture. The inflating of the balloon portions preferably includes conveying a fluid through a tube extending through the natural body opening into the natural body cavity.

A surgical method pursuant to a further embodiment of the present invention comprises inserting a first medical instrument into a patient via a natural body opening and a hollow body organ, inserting a second medical instrument through an opening formed in the skin surface of the patient, and manipulating the first medical instrument and the second medical instrument from outside the patient to effectuate a surgical operation on an organ inside the patient.

Typically, the second medical instrument is a laparoscopic instrument inserted through a trocar sleeve or laparoscopic cannula disposed in the opening formed in the skin surface of the patient.

One of the instruments may be an endoscope, this term being used in ageneric senseto include flexible endoscopes and rigid endoscopes such as laparoscopes and sigmoidoscopes.

A surgical method comprises, pursuant to yet another embodiment of the present invention, inserting a medical instrument into a patient via a natural body opening and a hollow body organ, inserting a sealing port through an opening formed in the skin surface of the patient, inserting a hand through the sealing port into an abdominal cavity of the patient, and manipulating the first medical instrument from outside the patient and using the hand inside the patient to effectuate a surgical operation on an organ inside the patient.

A surgical method comprises, in accordance with yet a further embodiment of the present invention, (a) inserting distal end portion a surgical instrument into hollow body organ of a patient via a natural body opening, (b) manipulating the instrument from outside the patient to form a small hole in a wall of the hollow body organ, (c) inserting a distal end portion of a medical instrument into the patient via the natural body opening, the hollow organ, and the hole, (d) manipulating the medical instrument from outside to patient to perform a medical procedure on the patient, (e) removing the medical instrument from the patient via the hole, the hollow body organ and the natural body opening, (f) terminating the surgical method by removing all medical instruments from the patient, and (g) leaving the hole unclosed upon the terminating of the surgical method.

This procedure may be performed, for instance, through the urinary bladder, where a small hole is eventually self-sealing and where the leakage of organ contents, namely, urine, into the abdominal cavity poses no threat or danger to the patient. Any urine leaked into the abdominal cavity is absorbed by the body. Such a procedure would be effective in a tubal ligation procedure, where nothing of substantial size need pass through the wall of the bladder.

DETAILED DESCRIPTION

Figure 1:
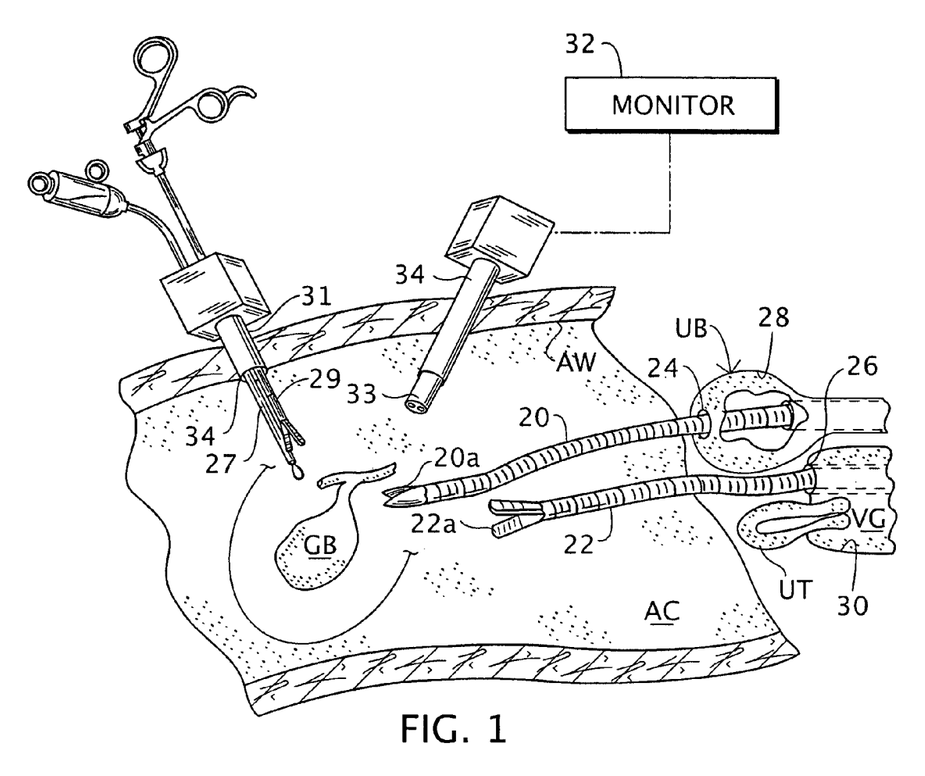
FIG. 1 is a schematic cross-sectional view of a patient's abdominal cavity showing a combined laparoscopic and transorgan surgical procedure in accordance with the present invention.

As depicted in FIG. 1, a surgical operation via natural body cavity as described in U.S. Pat. Nos. 5,297,536 and 5,458,131 may be carried out in conjunction with more conventional laparoscopic access procedures. For example, a surgical operation in the abdominal cavity AC such as removal of a gall bladder GB may be implemented via simultaneous access to the abdominal cavity via the urinary bladder UB and the vagina VG, as well as via an instrument inserted through the abdominal wall AW. (The uterus is represented at UT.)

FIG. 1 shows distal ends portions of two surgical instruments 20 and 22 such as a forceps and an ablation tool entering the abdominal cavity AC via openings 24 and 26 artificially formed in walls 28 and 30 of the bladder UB and the vagina VG via, for example, an incising instrument as described in U.S. Pat. Nos. 5,297,536 and 5,458,131. Instruments 20 and 22 have distal ends provided with operative tips 20a and 22a that are controlled from outside the patient via actuators (not shown) provided at the proximal ends of the instruments. The manipulation of these instruments 20 and 22 from outside the patient is witnessed via an image displayed on a video monitor 32 in response to a signal from an endocope (e.g., a laparoscope 33) partially inserted into the abdominal cavity AC via a cannula 35 disposed in and traversing the abdominal wall AW, for instance, at the umbilicus. Multiple instruments 27 and 29 may be deployed laparoscopically through a common incised opening 34 in abdominal wall AW via a multiport cannula 31, as disclosed in U.S. Pat. No. 5,183,471. Alternatively or additionally, other incisions (not shown) may be formed in the abdominal wall AW for enabling access to abdominal cavity AC by other laparoscopic instruments (not shown). Also, a distal end portion of a flexible endoscope (not shown) may be inserted into the abdominal cavity AC via the urinary bladder UB, the vagina VG (and the pouch of Douglas) or via another natural body cavity or lumen as defined by an organ such as the stomach (not shown) or the colon (not shown).

Figure 2A:
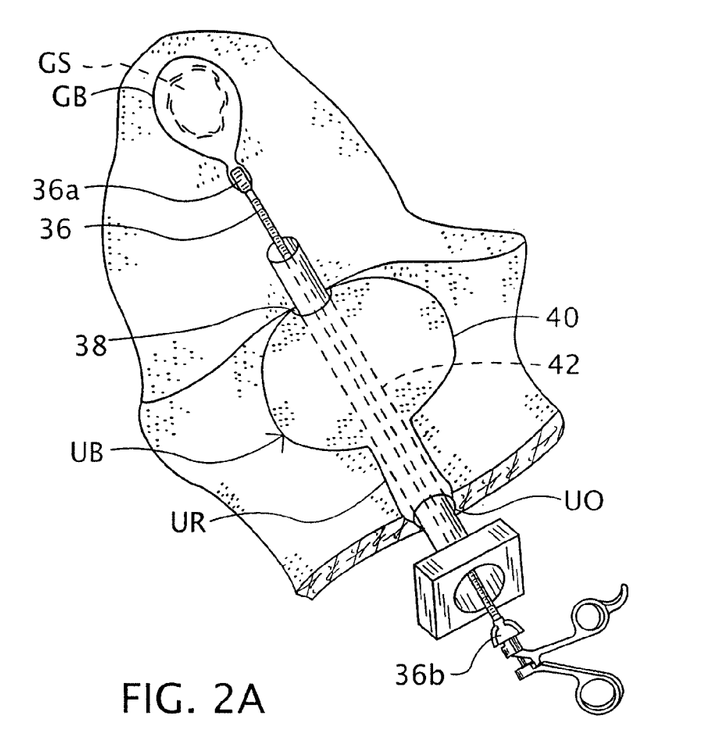
FIGS. 2A-2H are schematic cross-sectional views, some partially broken away, of a patient including the patient's urinary bladder, showing successive stages in the removal of an organ such as a gall bladder through the urinary bladder.
Figure 2B:
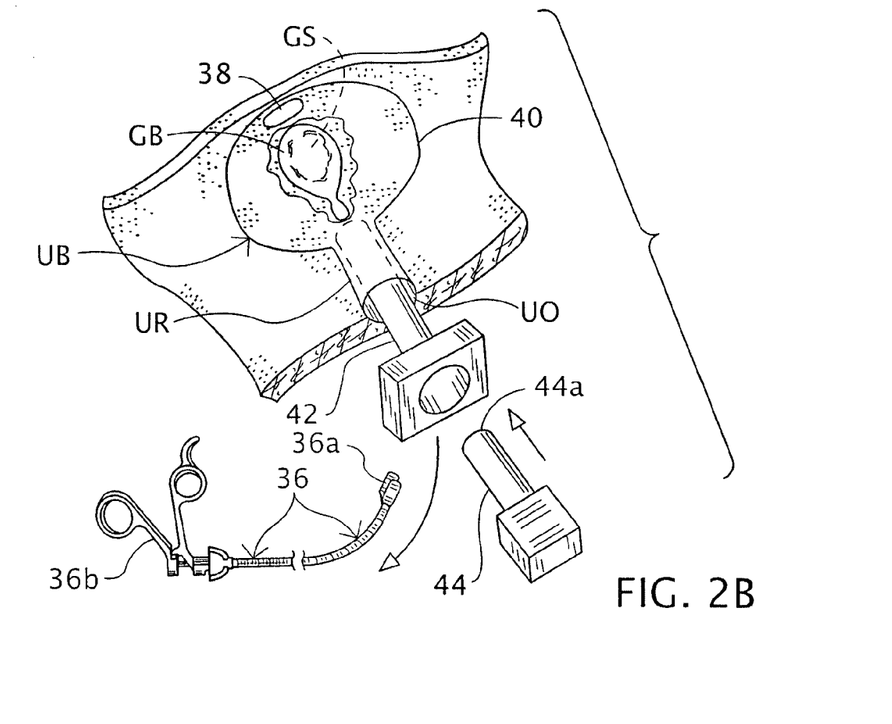

As illustrated in FIG. 2A, an internal organ such as the gall bladder GB is excised from a patient by a procedure as described in U.S. Pat. Nos. 5,297,536 and 5,458,131, which are incorporated by reference herein. A flexible distal end portion of an elongate grasper or forceps 36 having an operative tip 36a and an actuator 36b is inserted through a natural body opening such as the urethra UR, through the urinary bladder UB and an opening or hole 38 incised in the wall 40 of the urinary bladder. Grasper 36 may be inserted through a tubular guide member 42 that is in turn disposed in the urethra UR, the urinary bladder UB and opening or hole 38. A surgeon operates actuator 36b of grasper 36 from outside the patient to pull the excised gall bladder GB, together with one or more substantially sizes stones GS therein, through opening or hole 38 into urinary bladder UB, as shown in FIG. 2B. Grasper 36 is then removed from the patient and the distal end portion of a stone fractionating device or fragmenter 44 such as an ablation instrument, a morsellator, a laser wand or tool, an ultrasonic probe or device, or a set of crushing jaws, is inserted into urinary bladder UB.

Figure 2C:
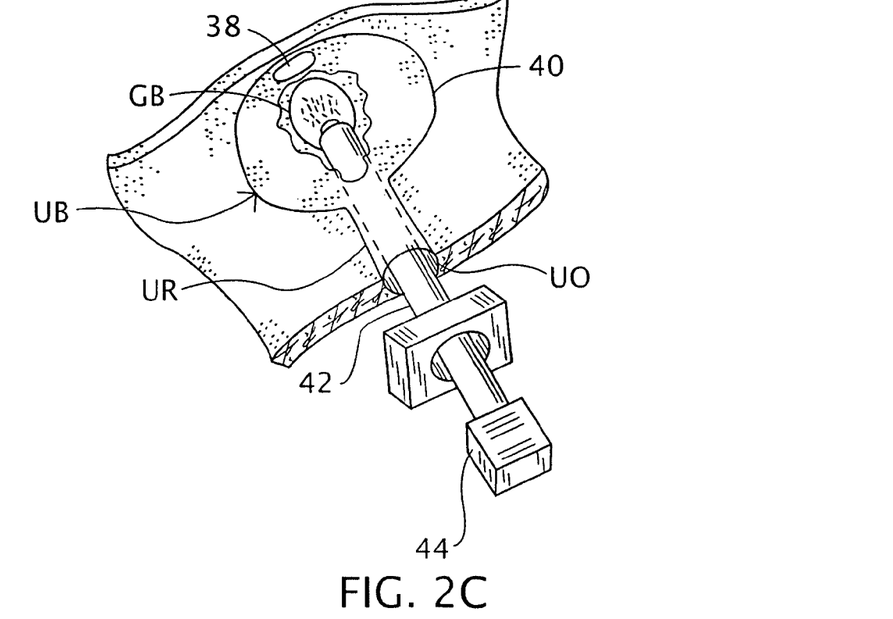
Figure 2D:
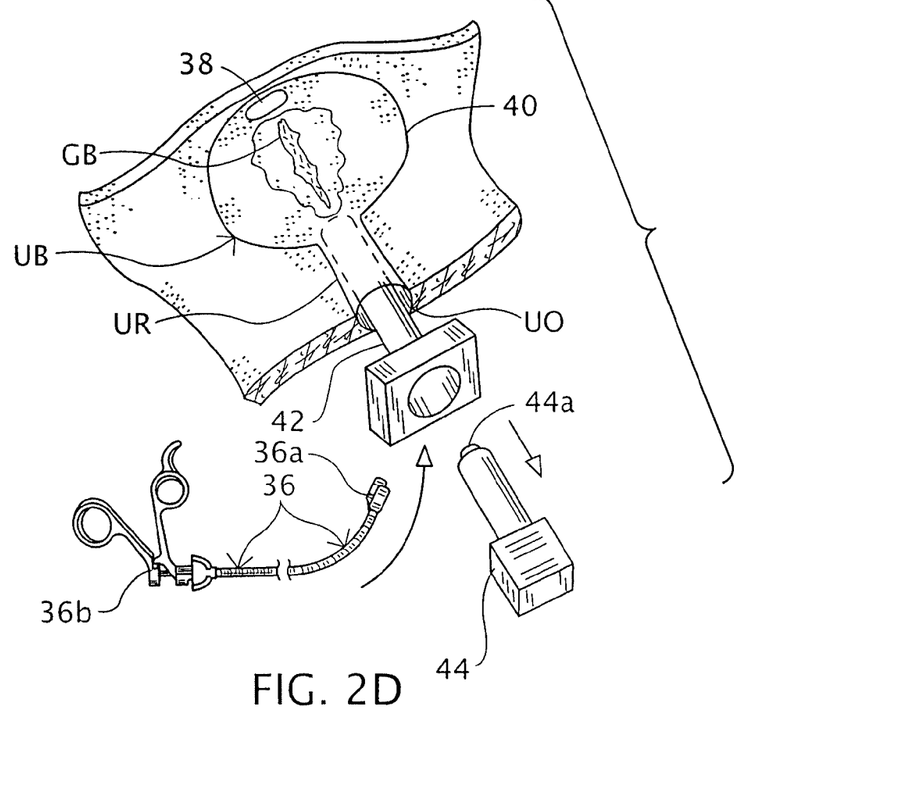
Figure 2E:
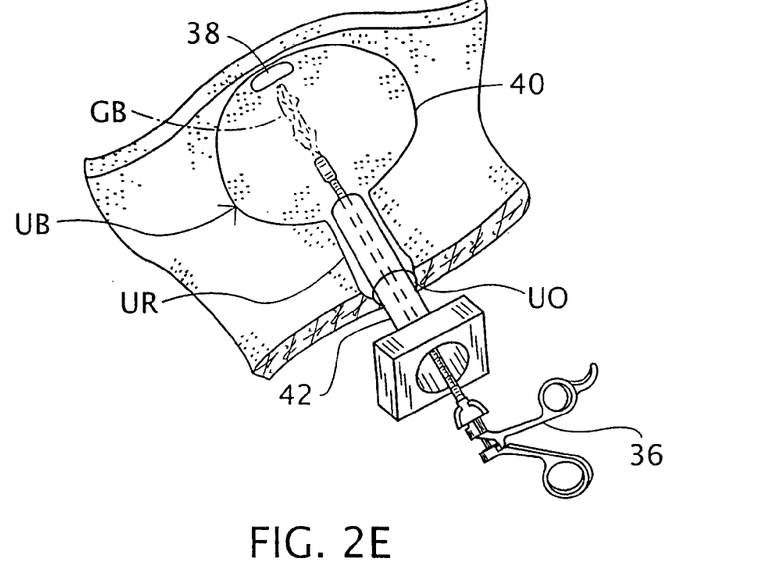

As depicted in FIG. 2C, the distal end portion of fractionating device or fragmenter 44, including an operative tip 44a, is inserted into the excised gall bladder GB inside the urinary bladder. Operative tip 44a is actuated from outside the patient to pulverize the gall stone(s) GS in the gall bladder GB. Thereafter, as indicted in FIG. 2D, the fractionating device or fragmenter 44 is removed from the patient and the grasper 36 is reinserted in to the urinary bladder UB through the urethra UR. The surgeon then manipulates the actuator 36b of grasper 36 to cause the operative tip 36a to entrain or grip the excised gall bladder GB inside the urinary bladder UB (FIG. 2E) and to pull the entrained gall bladder GB, together with the pulverized gall stone material, out of the urinary bladder UB via the urethra UR (FIG. 2F) and the urethral orifice UO, a natural body opening.

Figure 2F:
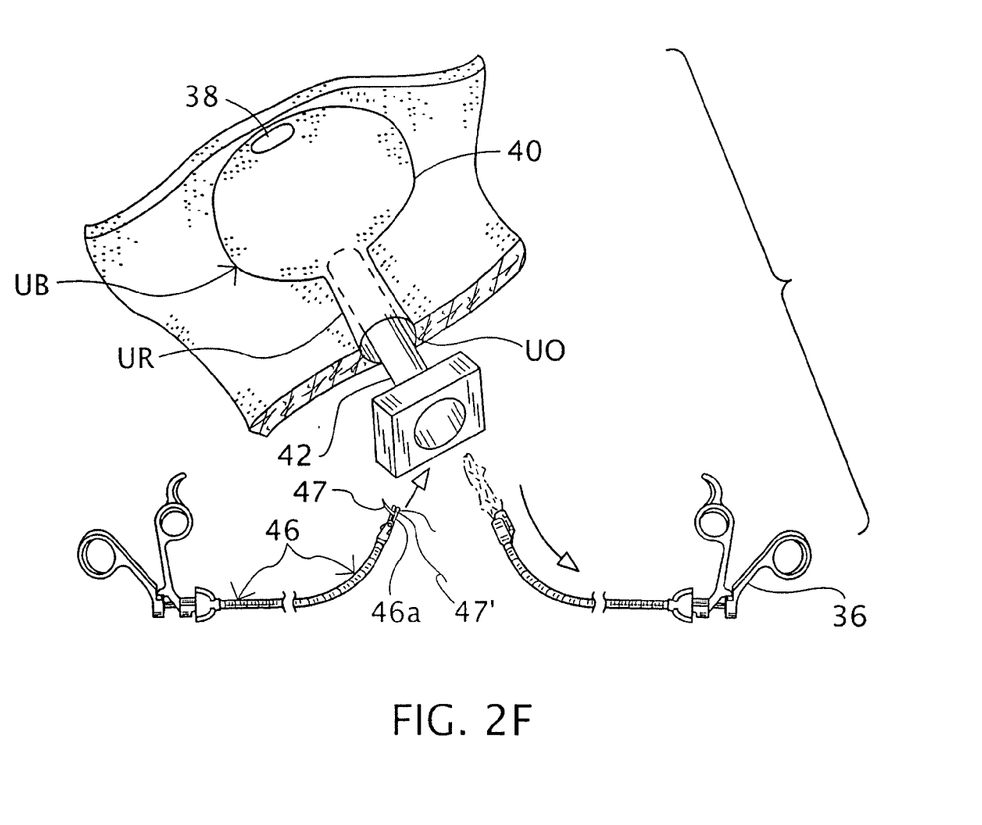
Figure 2G:
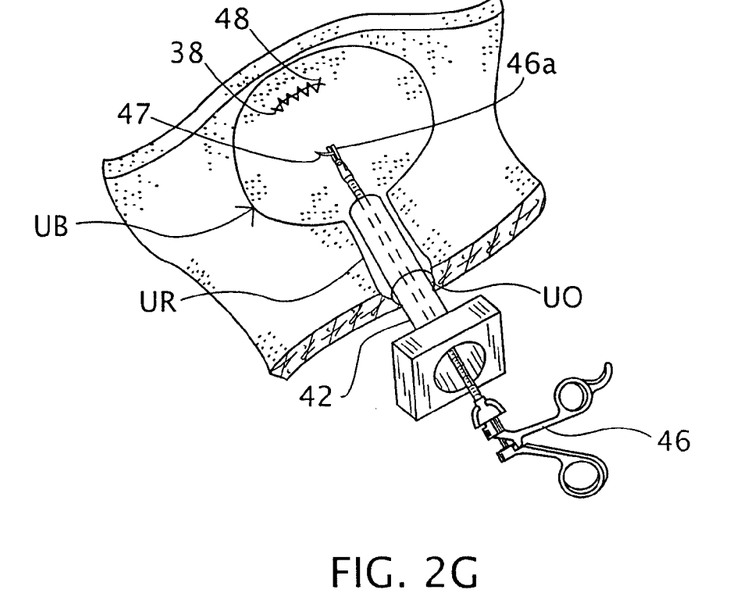
Figure 2H:
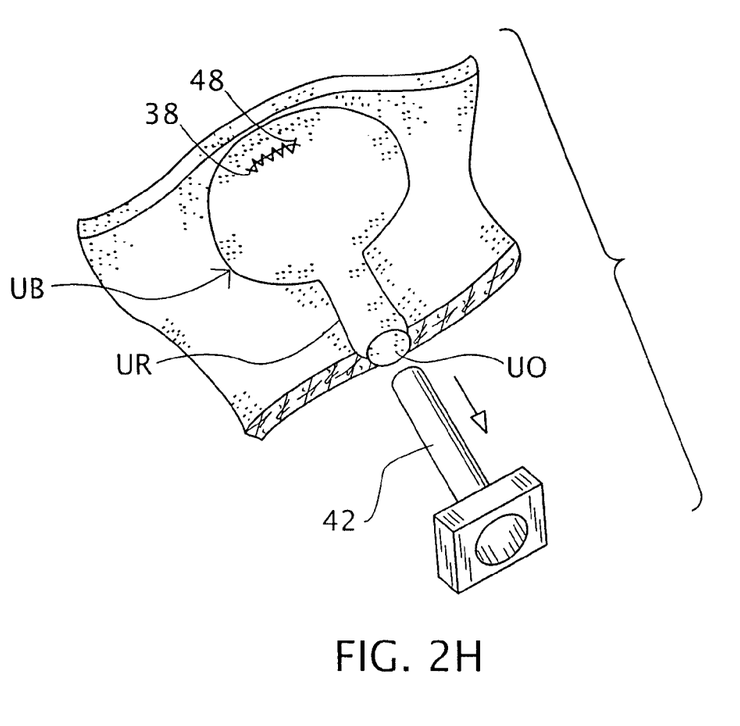

A distal end portion of a suturing or stapling instrument 46, including an operative tip 46a, is then inserted through the urethra UR into the gall bladder and operated to insert sutures or staples 48 in the wall 40 of the urinary bladder UB to close the artificial (not natural) opening or hole 38, as shown in FIG. 2G. FIG. 2F shows instrument 46 as a grasper holding a suture needle 47 and suture thread 47'. Other kinds of closure devices such as ligation bands, adhesively attached patches, or adhesive masses will be available to those skilled in the art. All instruments, e.g., tubular guide member or sleeve 42, are subsequently removed from the patient, as indicated in FIG. 2H.

As disclosed in U.S. Pat. Nos. 5,297,536 and 5,458,131, the foregoing procedure may be carried out by a surgeon who visually monitors the distal tips of the deployed instruments and the internal body tissues of the patient via one or more endoscopes. Distal end portions of the endoscopes may be inserted through natural body openings and the natural body cavities of hollow internal organs, as discussed in the patents. In this case, an endoscope is inserted through urethra UR and extends into bladder UB for enabling a visual inspection of ongoing surgical operations in that hollow organ.

In a specialized kind of procedure carried out through the urinary bladder, it may not be necessary to close the hole 38 in bladder wall 40. An example of such a procedure is a tubal ligation where small clips are inserted into a person's abdominal cavity through hole 38 and then placed around fallopian tubes (in the case of a female patient). In some cases, it may not be necessary to suture or staple or otherwise close hole 38. The hole may be small enough to eventually close on its own. Any urinary leakage into the abdominal cavity is naturally and harmlessly absorbed by the body.

Figure 3:
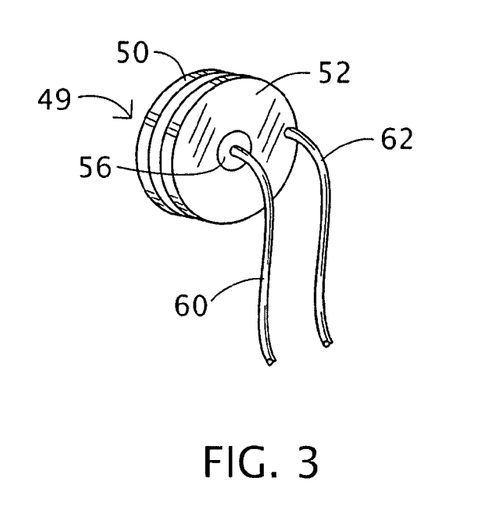
FIG. 3 is a schematic perspective view of a surgical port device in accordance with the present invention.
Figure 4:
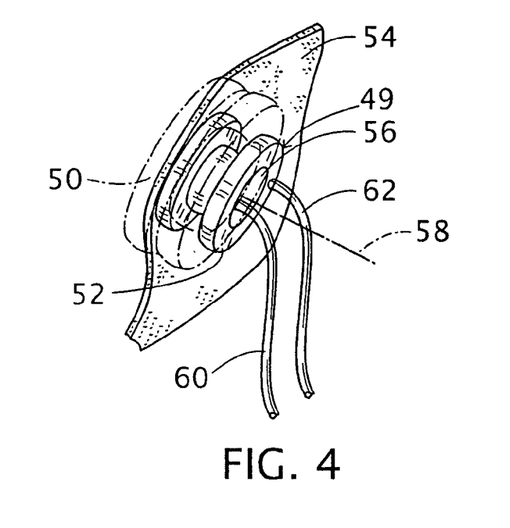
FIG. 4 is a schematic perspective view of the surgical port device of FIG. 3A, showing the device sandwiching a wall of a hollow organ, in accordance with the present invention.

As illustrated in FIGS. 3 and 4, a surgical port device 49 comprises two connected annular or toroidal balloons 50 and 52 each expandable from a collapsed configuration (solid lines in FIG. 4) to an inflated configuration (FIG. 3 and phantom lines in FIG. 4) wherein outer surfaces of the balloons are in contact with one another along a plane defined by the wall 54 of a hollow internal body organ. Balloons 50 and 52 define a through aperture or passageway 56 with an axis 58 extending substantially perpendicularly to plane 54.

Preferably, balloons 50 and 52 are independently inflatable and are provided with respective inflation tubes 60 and 62. Alternatively, balloons 50 and 52 may be portions of the same balloon structure, defining respective lobes of a single chamber. In that case, only one inflation tube would be necessary.

Figure 5A:
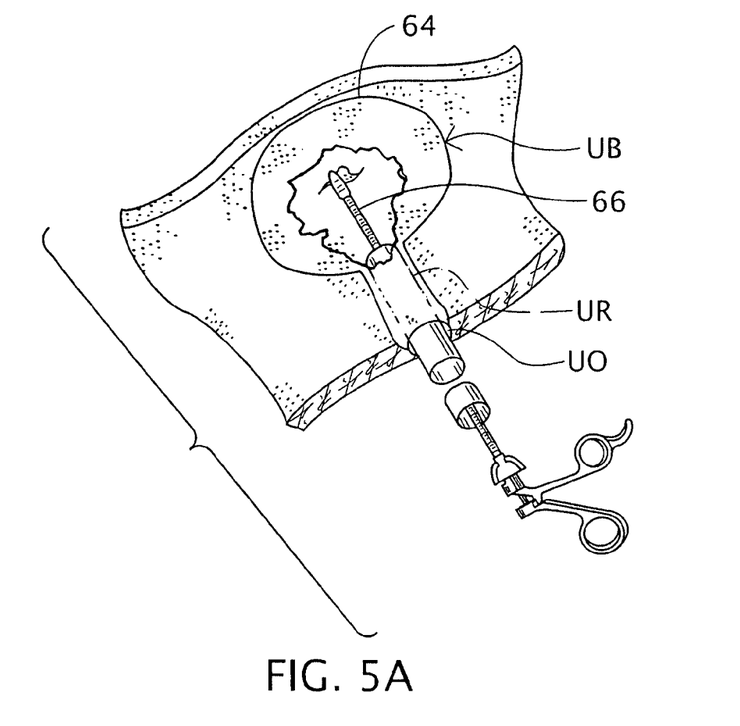
FIGS. 5A-5F are schematic cross-sectional views of a hollow internal organ of a patient, some views partially broken away, showing selected steps in the performance of an operation in the abdominal cavity of the patient via the hollow organ.
Figure 5B:
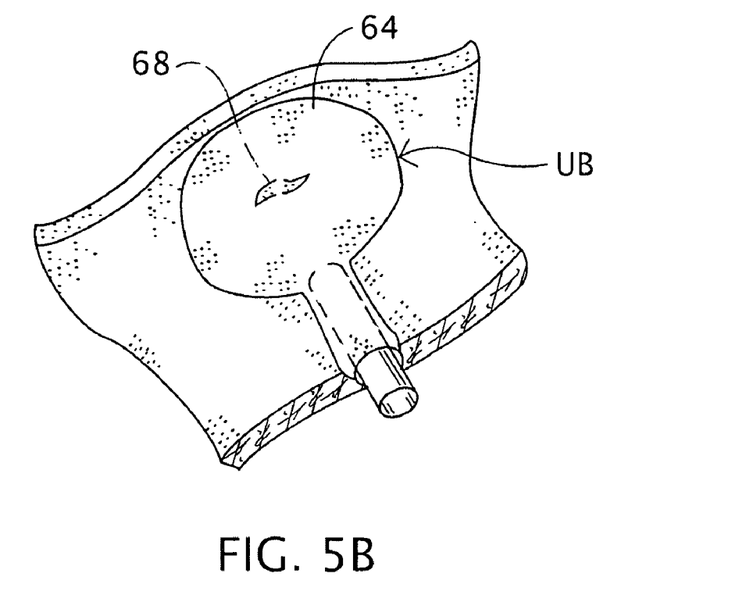
Figure 5C:
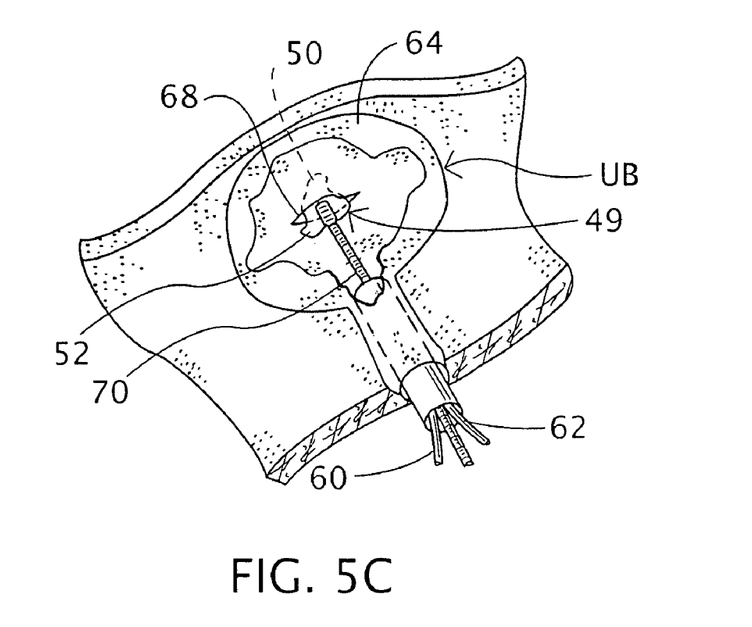
Figure 5D:
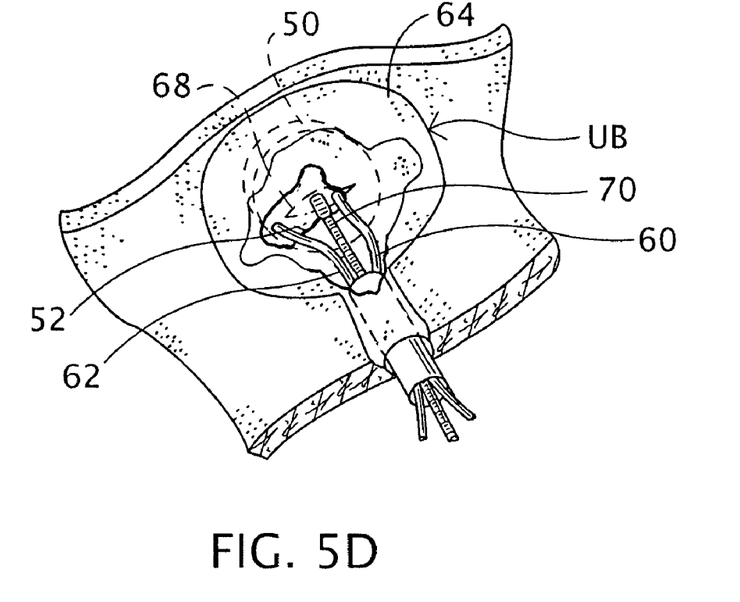

Any transorgan procedure described herein or in U.S. Pat. Nos. 5,297,536 and 5,458,131 may include the deployment of port device 49. A generic procedure will now be described with reference to FIGS. 5A-5F. A transvessicle port is formed in a wall 64 of a hollow internal body organ such as the urinary bladder UB by inserting an incising instrument 66 through a natural body opening such as the urethral orifice UO and the urethra UR into the natural body cavity defined by the respective hollow organ, in this case the urinary bladder UB (FIG. 5A). The incising instrument 66 is manipulated from outside the patient to form a hole or opening 68 in the wall 64 of the bladder UB (FIG. 5B). Surgical port device 49 is then inserted into the natural body cavity of the bladder UB via the urethra. The balloons 50 and 52 are in a collapsed configuration during this insertion operation. Subsequently, the deflated or collapsed surgical port device 49 is positioned by a grasper 70 in hole or opening 68 (FIG. 5C). With grasper 70 holding port device 49 in hole or opening 68, the distal balloon 50 is inflated by pumping a pressurizing fluid such as a saline solution or carbon dioxide through tube 60 (FIG. 5D). (Tubes 60 and 62 extend back out through the urethra UR.)

Figure 5E:
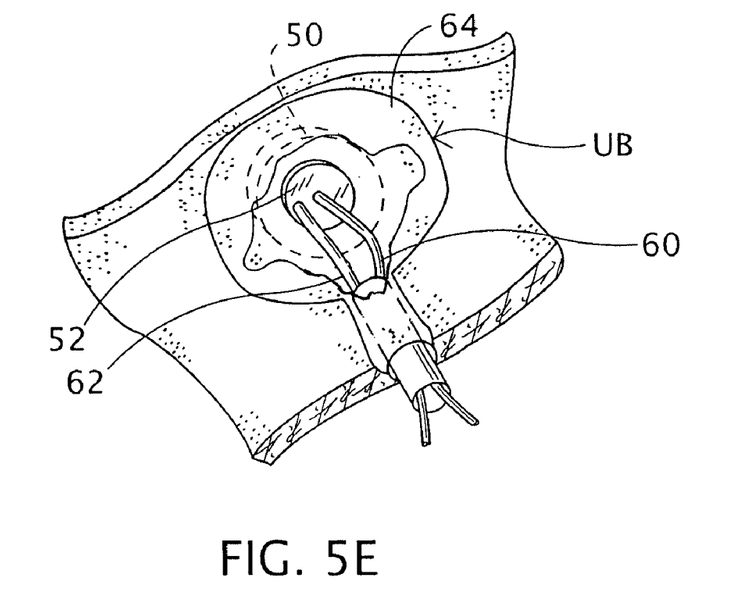
Figure 5F:
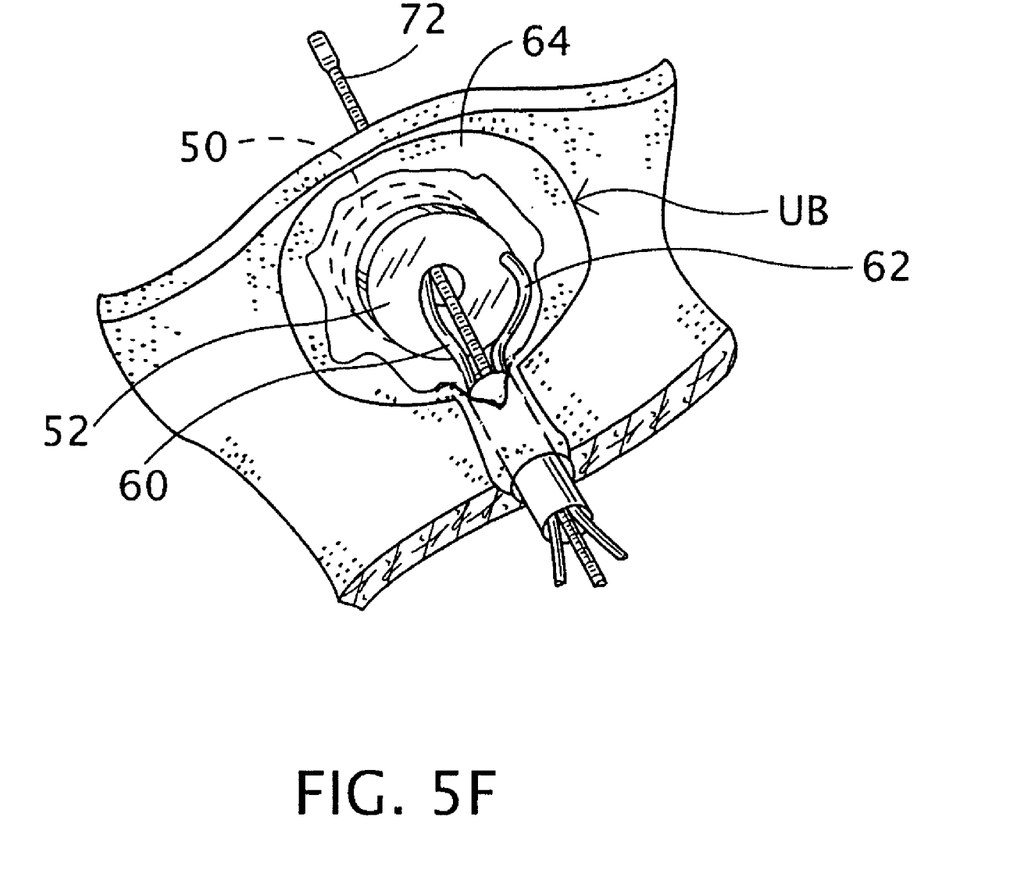

Grasper 70 is manipulated from outside the patient to properly position the port device 49 so that the inflated distal balloon 50 is in contact with an outer surface of wall 64, i.e., a surface facing into the abdominal cavity. A tensile force is placed on grasper 70 to pull inflated distal balloon 50 against the bladder wall 64. At that time, the proximal balloon 52 is inflated by pumping a pressurizing fluid such as a saline solution or carbon dioxide through tube 62. FIG. 5E shows proximal balloon 52 in a partially inflated configuration. Upon completed inflation of proximal balloon 52, grasper 70 releases port device 49. (Grasper 70 is omitted from FIG. 5E for clarity.) At that time, a distal end portion of grasper 70 or another instrument 72 may be inserted into the abdominal cavity of the patient via aperture or passageway 56 (FIG. 5F). Subsequently, after the performance of a medical diagnostic or treatment procedure inside the abdominal cavity via urinary bladder UB, balloons 50 and 52 are deflated, for instance, by cutting or puncturing the balloons or by sucking the fluid back out through tubes 60 and 62. After balloon deflation, port device 49 is removed from hole or opening 68. The surgeon may accomplish this removal by simply and gently pulling on tubes 60 and/or 62, Alternatively, the surgeon may utilize grasper 70 to pull the deflated port device 49 from the bladder UB.

Figure 6:
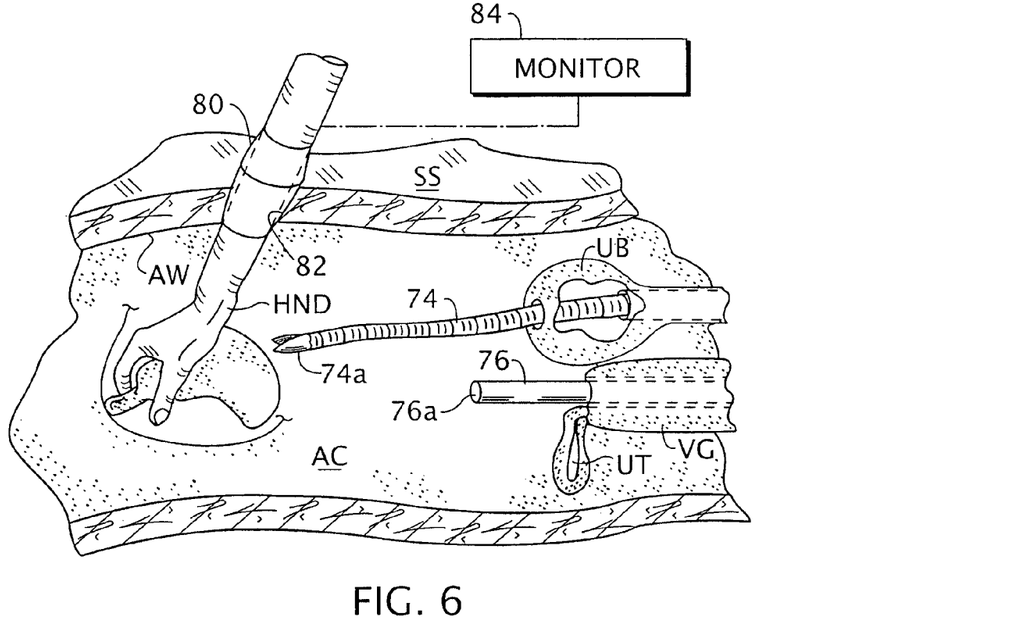
FIG. 6 is a schematic cross-sectional view of a patient's abdominal cavity showing a combined laparoscopic and transorgan surgical procedure in accordance with the present invention.

As depicted in FIG. 6, distal end portions of elongate medical instruments 74 and 76, including operative tips 74a and 76a, are inserted into a patient's abdominal cavity AC through via the natural body openings of the urethral and vaginal orifices (not shown), the natural body cavities of the urinary bladder UB and vagina VG, and artificial (surgeon-incised) openings 76 and 78 in the walls of the bladder UB and vagina VG. In addition, a sealing port 80 is inserted through an opening 82 formed in the skin surface SS of the patient. During an ensuing intra-abdominal procedure, the surgeon inserts a hand HND through the sealing port 80 into the abdominal cavity AC of the patient. Medical instruments 74 and 76 are manipulated from outside the patient, while the surgeon uses his hand HND inside the patient to effectuate a surgical operation on an organ (e.g. gall bladder GB) inside the patient. FIG. 6 shows instrument 76 as an endoscope or camera-carrying instrument. A monitor or video screen 84 displays the image captured by endoscope or camera 76. The patient's uterus is omitted from FIG. 6 for purposes of clarity.

Figure 7:
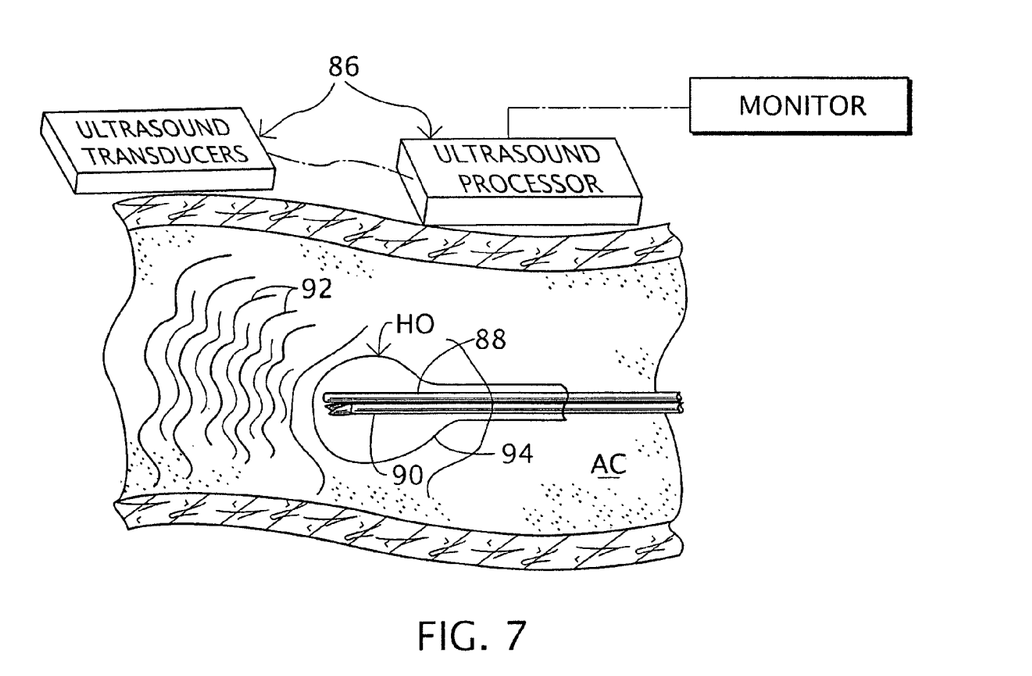
FIG. 7 is a schematic cross-sectional view of a patient's abdominal cavity showing another transorgan surgical procedure in accordance with the present invention.

Prior to cutting of an incision in a wall of a hollow organ pursuant to the procedures discussed hereinabove and in U.S. Pat. Nos. 5,297,536 and 5,458,131, it is recommended to inspect the area of the contemplated incision to determine whether there is another organ in the abdominal cavity AC lying against the wall of the hollow organ. If so, incising the hollow organ would also inadvertently cut the other organ. This inspection may be carried out via a scanning device such as an X-ray machine, CAT scanner, an MRI machine, or an ultrasound apparatus 86 (FIG. 7). Alternatively, as depicted in FIG. 7, an ultrasound probe 88 may be inserted into the hollow organ HO through a natural body opening, together with an incising instrument 90. If the ultrasonic pressure waves 92 generated by the ultrasound probe 88 fail to reveal another organ on the opposite side of a wall 94 of the hollow organ HO, the surgeon uses incising instrument 90 to form a hole or opening in the organ wall 94. Ultrasound probe 88 and incising instrument 90 may be integrated into a single instrument for this purpose.

Instruments for accomplishing the above-described surgical procedures may be marketed as assemblies in packages containing two or more instruments or devices for each specific procedure.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method comprising:
   inserting a surgical incising instrument through a patient's urethra into the patient's urinary bladder;
   using said surgical incising instrument to cut an opening through a wall of said bladder;
   inserting a medical instrument through said urethra, said bladder and said opening;
   subsequently manipulating said medical instrument from outside the patient to perform an operation on an organ inside the abdominal cavity of the patient, said medical instrument extending through said urethra, said bladder and said opening into the abdominal cavity during the manipulating of said medical instrument; and
   withdrawing said medical instrument from the patient through said opening, said bladder, and said urethra.

2. The method defined in claim 1 wherein said surgical instrument and said medical instrument are different instruments.

3. The method defined in claim 1, wherein the manipulating of said medical instrument includes using said medical instrument from outside the patient to sever at least a portion of said organ, further comprising withdrawing the severed organ portion out of the patient through the urinary bladder and the urethra.

4. The method defined in claim 3, further comprising inserting a distal end portion of a medical tool through the urethra and the urinary bladder and operating said medical tool from outside the patient to fractionate material of said severed organ portion prior to the withdrawing of the severed organ portion out of the patient.

5. The surgical method defined in claim 4 wherein said medical tool is taken from the group consisting of an ablation instrument, a morsellator, a laser tool, and an ultrasound device.

6. The method defined in claim 1 wherein said organ is taken from the group consisting of the uterus, the gall bladder, and a kidney.

7. The surgical method defined in claim 6 wherein said organ is the gall bladder, said material including one or more gall stones, further comprising inserting a distal tip of said medical tool into the gall bladder prior to the operating of said medical tool to fractionate said gall stones.

8. The method defined in claim 1, further comprising:
providing a surgical port device;
inserting said device through the patient's urethra into the urinary bladder;
subsequently disposing said port device in said opening to keep the same open, said port device defining an aperture surrounded by said opening and coaxial therewith, a distal end portion of said medical instrument being inserted through said aperture.

9. The method defined in claim 8 wherein said port device comprises at least two balloon portions, said port device being inserted through the patient's urethra in a collapsed configuration, said port device being disposed in said opening so that said balloon portions are positioned on opposite sides of said wall, the disposing of said port device in said opening including inflating said balloon portions to hold said port device in said wall and to define said aperture.

10. The surgical method defined in claim 9 wherein the inflating of said balloon portions includes conveying a fluid through a tube extending through the urethra into the bladder.

11. A surgical method comprising:
forming an artificial opening in a wall of a patient's urinary bladder;
inserting a distal end portion of a medical instrument through the patient's urethra, said bladder and said opening;
subsequently manipulating said medical instrument from outside the patient to perform an operation on an organ inside the abdominal cavity of the patient and different from said urinary bladder, said distal end portion of said medical instrument extending through said urethra, said bladder and said opening into the abdominal cavity during the manipulating of said medical instrument; and
subsequently withdrawing said medical instrument from the patient through said opening, said bladder, and said urethra.

12. The method defined in claim 11 wherein the forming of said opening includes inserting an incising instrument into said bladder via said urethra and operating said incising instrument from outside the patient.

13. The method defined in claim 12 wherein said incising instrument and said medical instrument are different instruments.

14. The method defined in claim 11, wherein the manipulating of said medical instrument includes using said medical instrument from outside the patient to sever at least a portion of said organ, further comprising withdrawing the severed organ portion out of the patient through the urinary bladder and the urethra.

15. The method defined in claim 14, further comprising inserting a distal end portion of a medical tool through the urethra and the urinary bladder and operating said medical tool from outside the patient to fractionate material of said severed organ portion prior to the withdrawing of the severed organ portion out of the patient.

16. The surgical method defined in claim 15 wherein said medical tool is taken from the group consisting of an ablation instrument, a morsellator, a laser tool, and an ultrasound device.

17. The method defined in claim 11 wherein said organ is taken from the group consisting of the uterus, the gall bladder, and a kidney.

18. The surgical method defined in claim 17 wherein said organ is the gall bladder, said material including one or more gall stones, further comprising inserting a distal tip of said medical tool into the gall bladder prior to the operating of said medical tool to fractionate said gall stones.

19. The method defined in claim 11, further comprising:
providing a surgical port device;
inserting said device through the patient's urethra into the urinary bladder;
subsequently disposing said port device in said opening to keep the same open, said port device defining an aperture surrounded by said opening and coaxial therewith, a distal end portion of said medical instrument being inserted through said aperture.

20. The method defined in claim 19 wherein said port device comprises at least two balloon portions, said port device being inserted through the patient's urethra in a collapsed configuration, said port device being disposed in said opening so that said balloon portions are positioned on opposite sides of said wall, the disposing of said port device in said opening including inflating said balloon portions to hold said port device in said wall and to define said aperture.

21. The surgical method defined in claim 20 wherein the inflating of said balloon portions includes conveying a fluid through a tube extending through the urethra into the bladder.

\* \* \* \* \*